United States Patent [19]
Eichhorn et al.

[11] 4,320,769
[45] Mar. 23, 1982

[54] UNIVERSAL HOLDER FOR BLOOD COLLECTING TUBES

[75] Inventors: Edward C. Eichhorn, Dumont; Edward L. Nugent, North Caldwell; Shenoda S. Megahed, Lyndhurst, all of N.J.

[73] Assignee: Becton, Dickinson and Company, Paramus, N.J.

[21] Appl. No.: 907,757

[22] Filed: May 19, 1978

[51] Int. Cl.³ .............................................. A61B 5/00
[52] U.S. Cl. ................................................. 128/763
[58] Field of Search .................. 128/2 F, 2 G, 218 D, 128/220, 272, 276, DIG. 5, 760–765; 233/26; 206/306, 364, 365

[56] References Cited
U.S. PATENT DOCUMENTS
4,150,666  4/1979  Brush ................................ 128/2 F Primary Examiner—John D. Yasko

[57] ABSTRACT

A holder is provided for use with intravenous needle assemblies and evacuated tubes of various diameters used in conjunction with such assemblies. The holder has a threaded end for attachment of the needle assembly, and a body consisting of a barrel for insertion of evacuated tubes having resilient stoppers. Deformable ribs are provided within the barrel which enable the holder to accommodate tubes of varying sizes. The ribs may be tapered inwardly in the direction of the threaded tip to hold, center and guide the evacuated tubes.

24 Claims, 13 Drawing Figures

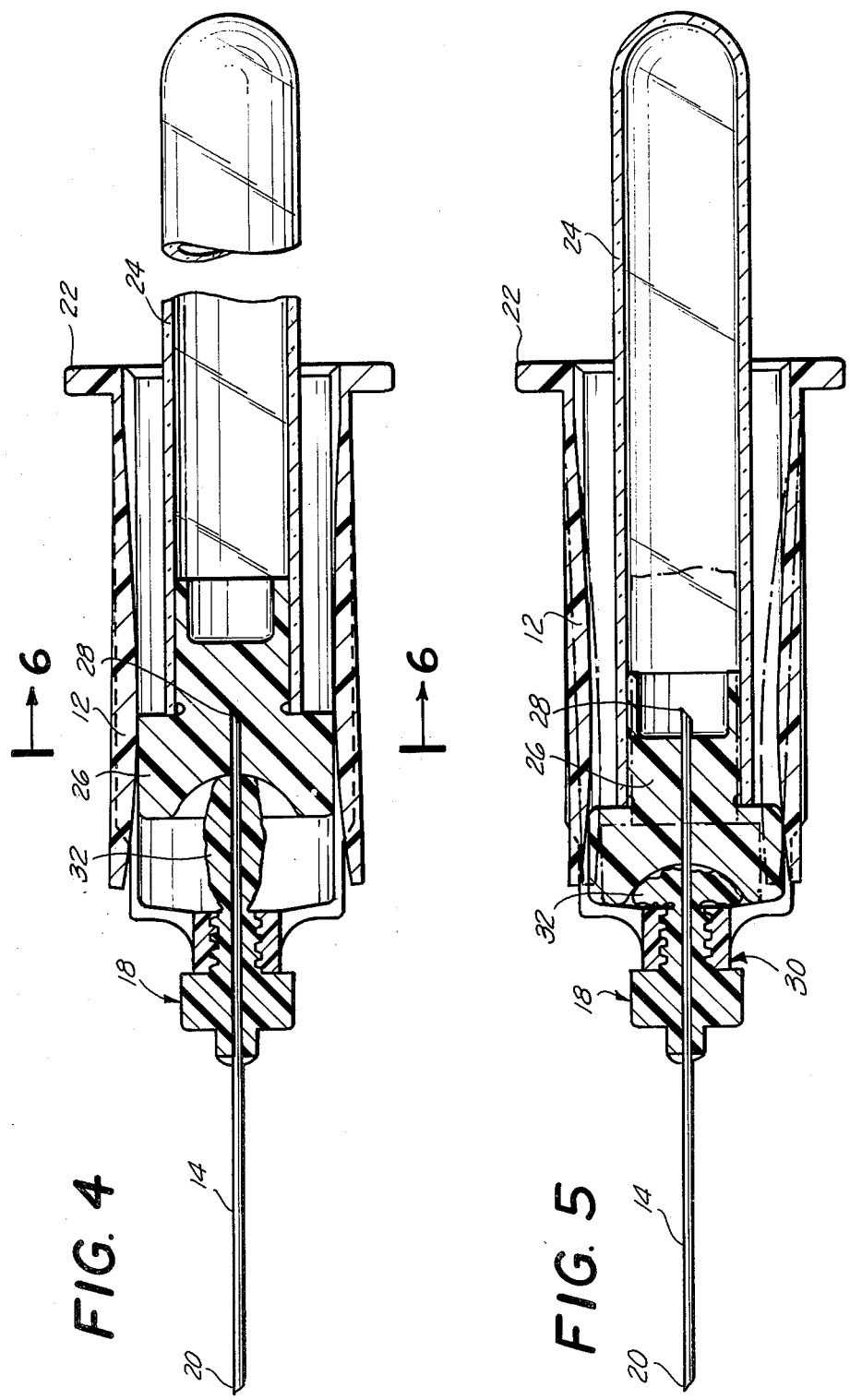

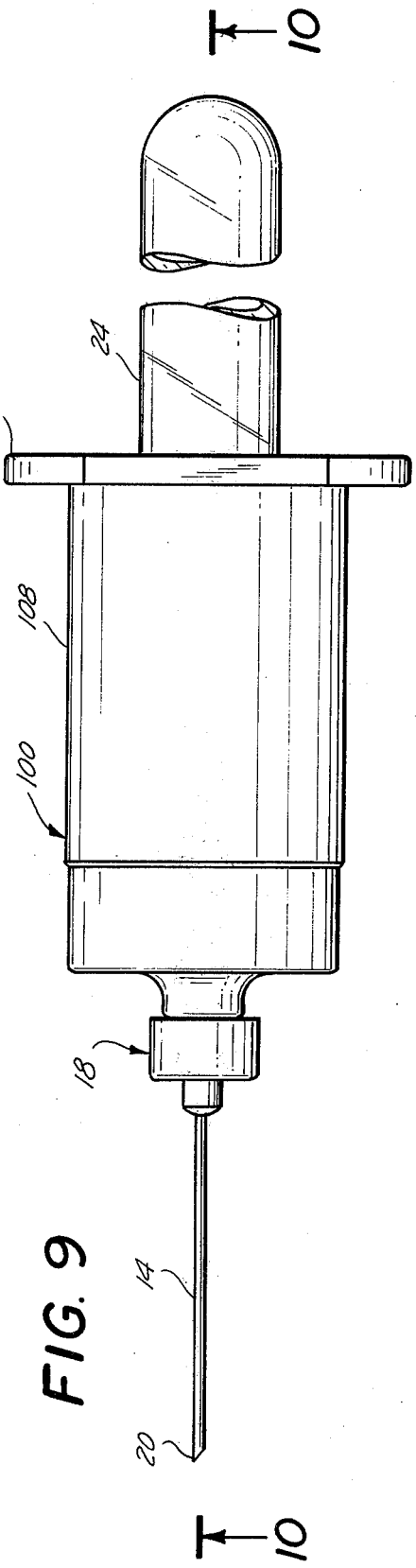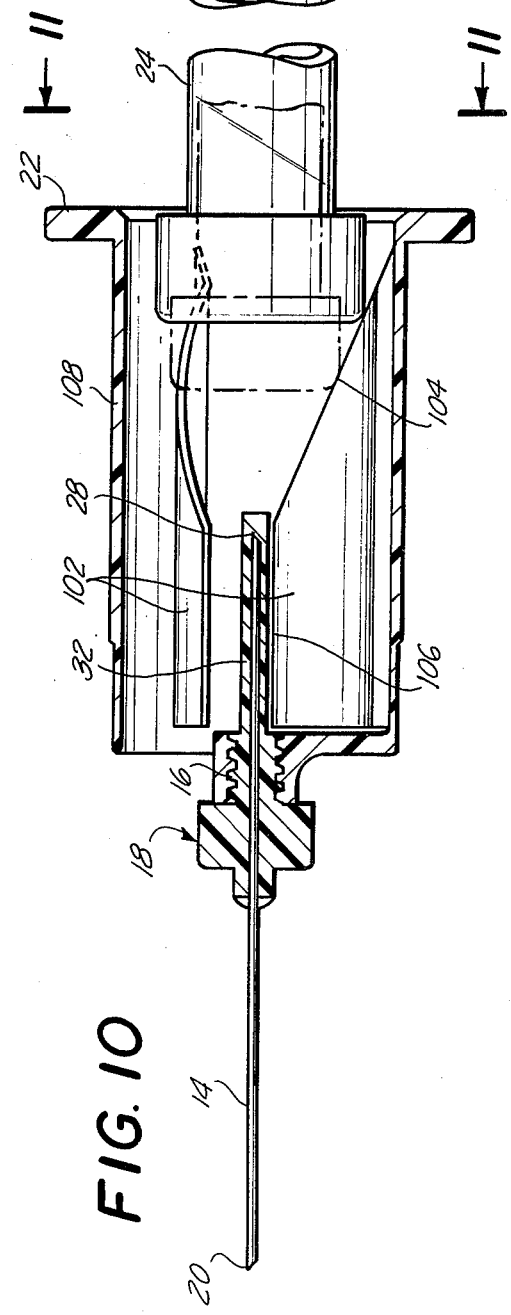

UNIVERSAL HOLDER FOR BLOOD COLLECTING TUBES

BACKGROUND OF THE INVENTION

The invention relates to the field of holders for multiple sampling needle assemblies and associated blood collection tubes.

A commonly used method for collecting blood is the employment of a needle assembly in conjunction with an evacuated container. The evacuated container provides the pressure differential necessary to facilitate flow and collection of the blood through the needle assembly into the container.

Known blood collection devices have employed needle assemblies having one end designed for venipuncture and another for puncture of the resilient closure of the evacuated tube. The needle assembly has a threaded portion allowing a holder to be attached thereon. An evacuated container is inserted within the holder unitl its closure is punctured by the appropriate end of the needle. Such a device is shown, for example, in commonly assigned U.S. Pat. No. 3,874,367.

Conventional holders do not allow for the insertion of all diameter sizes of collection tubes. As a result, to fill different sized tubes, a number of venipunctures must be made. It also requires the manufacture of different size holders to accommodate tubes of varying diameters, or to construct the closures of the tubes to fit within the holder properly. It would be most advantageous if a holder were designed to accommodate a number of differently sized tubes, as the above procedures would then be unnecessary.

SUMMARY OF THE INVENTION

With the above background in mind, it is among the primary objectives of the present invention to provide a multiple sampling needle assembly with a holder which will accommodate a number of different sized diameter fluid collection tubes with different sized closures, particularly those for collecting blood.

It is another object of the invention to provide an assembly which allows the filling of collection tubes of various diameters using only a single venipuncture.

Still another object of the invention is to provide a holder which will hold, center, and guide collection tubes.

These and other objectives are accomplished by providing a holder having one end adapted for attachment to a needle assembly, and the other adapted to receive blood collection tubes of different diameters. The barrel of the holder, into which the tubes are inserted, contains a plurality of deformable or deflectable resilient means (hereinafter referred to as ribs). These ribs hold the collection tubes by frictional contact, and flex proportionally to the diameter of the tube. In this manner, tubes of different diameters may be held by the same holder. The ribs may be arranged so that they are tapered in the direction of the needle assembly, or may be arranged in a spiral configuration. Both designs provide for effective centering, guiding, and holding of the collection tube.

When in use for various blood collection, the intravenous (IV) end of the needle is injected into the vein of a patient. An evacuated collection tube is inserted into the holder, and fluid communication is established between the IV needle and the interior of the tube. The pressure differential causes blood to fill the tube, and the tube is then withdrawn. To fill a second tube having a different diameter or different size closure, the procedure is identical and a second venipuncture is not needed.

The invention can be further understood from the following description and accompanying drawings.

BRIEF DESCRIPTION OF THE DRAWINGS

FIG. 4 is a similar view to FIG. 2 showing partial insertion of an evacuated tube;

FIG. 5 is a similar view to FIG. 4 showing the full insertion of two diameter sizes of evacuated tubes;

FIG. 9 is a side elevation view of a third embodiment of the invention;

FIG. 10 is a sectional view of the invention taken along line 10—10 of FIG. 9;

DETAILED DESCRIPTION OF THE INVENTION

Figure 1:
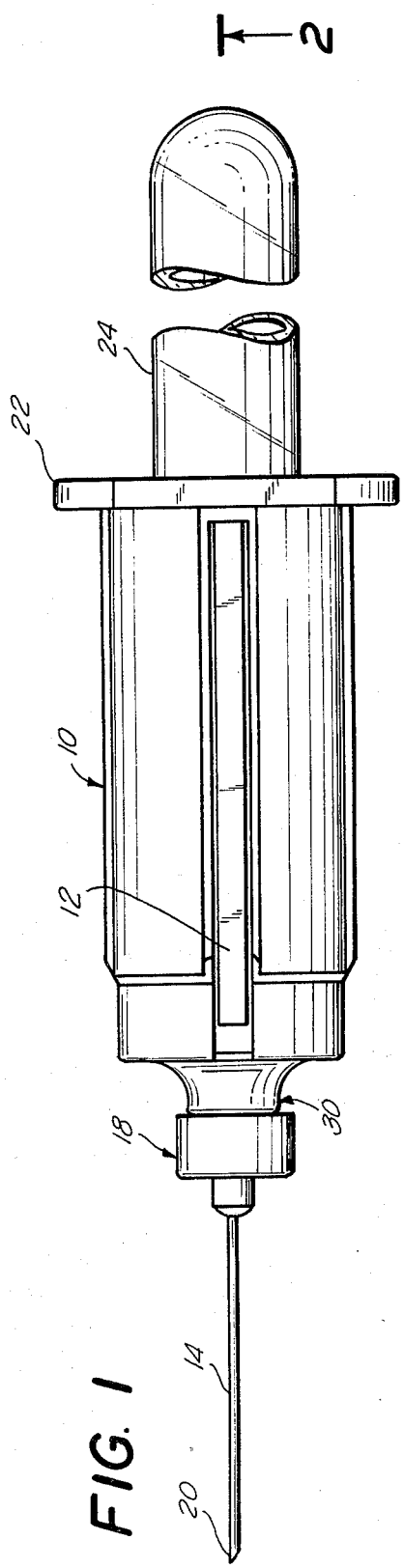
FIG. 1 is a side elevation view of the invention.

FIGS. 1-7 illustrate an embodiment of the invention as applied in conjuntion with an evacuated blood collection tube, such as a Vacutainer brand tube manufactured by Becton, Dickinson and Company of Rutherford, New Jersey. The universal holder 10 is made from a polymer such as polypropylene, although any suitable material will suffice. Flanges 22 are provided on one end to facilitate gripping of the holder, and threads 16 on the other end 30 for attachment of a needle assembly 18. Deformable ribs 12 are provided within the barrel of the holder 10 to frictionally engage the exterior surface of a resilient closure 26 of an evacuated tube 24.

The needle assembly 18 includes a cannula 14 attached thereto by epoxy or other suitable means. The cannula has a forward end 20 adapted for penetration of a vessel of the body, and a distal end 28 for puncturing the closure 26 of the evacuated tube 24. The distal end of the cannula may be covered by an elastic sleeve 32 which occludes the opening at 28 prior to full insertion of the tube within the holder. This prevents the dripping of blood when a vessel is penetrated by the cannula prior to the application of the collection tube.

Figure 2:
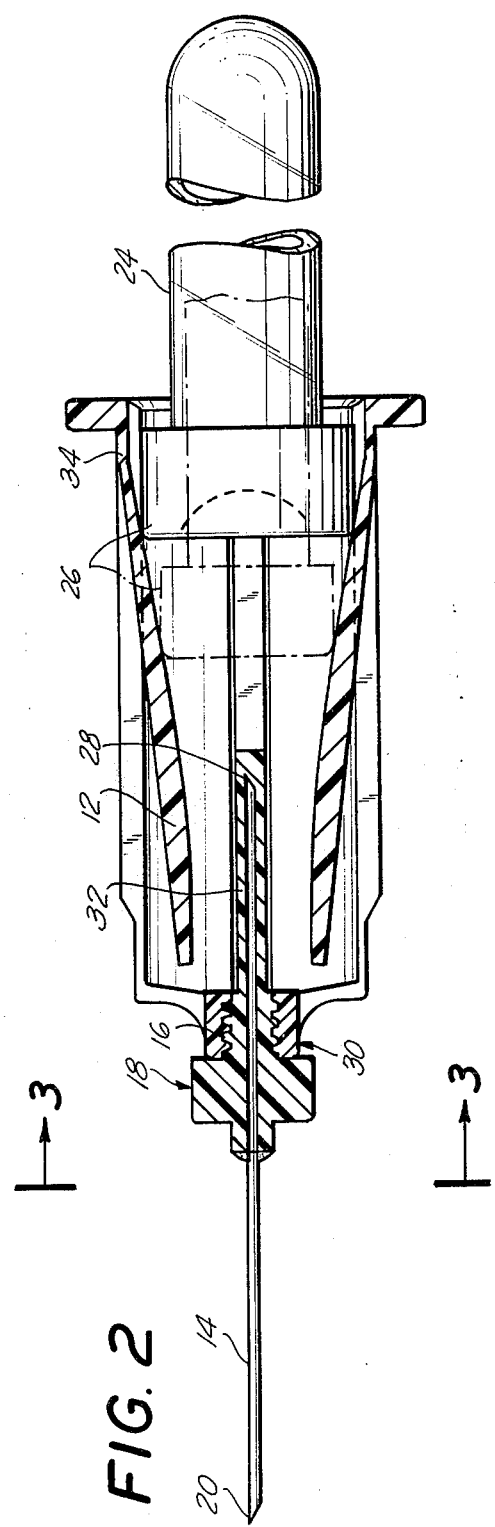
FIG. 2 is a sectional view taken along line 2—2 of FIG. 1.

The holder shown in FIGS. 1-7 includes deformable ribs which deflect about their points of attachment 34 to the holder 10. The ribs naturally assume a position as shown in FIG. 2 whereby they are angled inwardly in the direction of the needle assembly. This provides for easy insertion of evacuated tubes, and the frictional engagement thereof as their stoppers deflect the ribs outwardly. The natural resiliency of the plastic ribs creates the force exerted on the stoppers and/or tubes. When the tube is withdrawn, the ribs assume their natural position.

Figure 8:
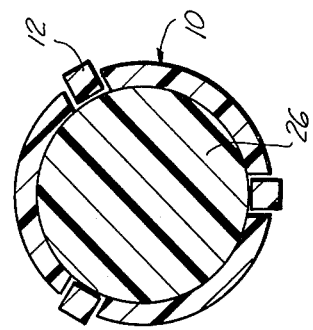
FIG. 8 is a cross-sectional view of an alternative embodiment of the apparatus shown in FIGS. 1-7, the holder having three ribs instead of four.

FIG. 8 shows a holder construction similar to that of FIGS. 1-7, the only difference being the provision of three ribs instead of four. This embodiment is also capable of centering and guiding a tube as it is inserted within the holder, in addition to frictionally engaging such tubes.

FIGS. 9-13 illustrate another embodiment of the invention. The same numberals are used for identifying similar parts as shown in FIGS. 1-8.

Holder 100 includes deformable ribs 102 which are attached to the inner surfaces of the barrel 108 of the holder. Both the holder and ribs are again of polymeric construction. As best shown in the lower rib of FIG. 10, the ribs have a tapered portion 104 which extends from near the distal end of the holder for approximately half the length of the barrel. Then remaining portion 106 of the rib has a surface which is substantially parallel to the walls of the holder. In this embodiment, the ribs are attached to the barrel walls for substantially their entire length.

Figure 13:
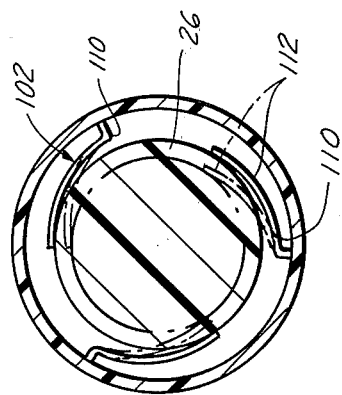
FIG. 13 is a cross-sectional view taken along line 13—13 of FIG. 12.
Figure 12:
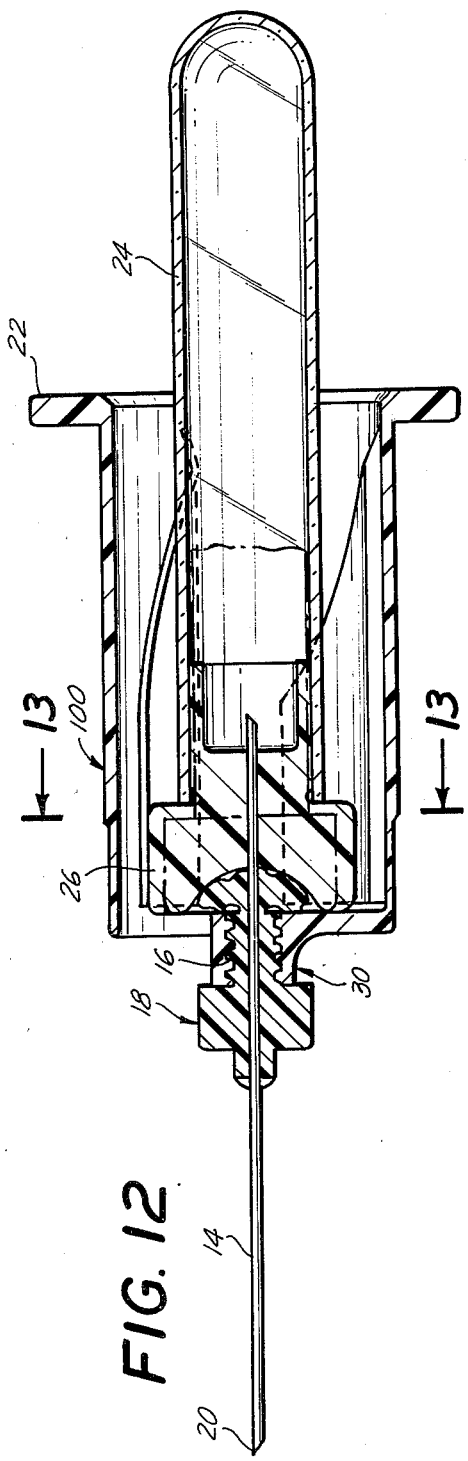
FIG. 12 is a sectional view of the invention showing the insertion of different diameter tubes.

FIGS. 10-13 illustrate the spiral configuration of the ribs 102. As a tube is inserted within the holder, the ribs flex along relatively sharp bends 110 from which the arcuate portions 112 of the ribs extend. The ribs naturally assume the positions shown in FIG. 11, and are deflected by various diameter tubes as shown in FIGS. 12 and 13. Tapering the ribs near the distal end of the holder facilitates insertion and centering of the tube.

All of the holders which have been described herein are designed to provide a number of functional advantages. The collection tubes are easily inserted within the holders, and are retained therein by frictional engagement of the resilient ribs. The ribs, due to their orientation, also center and guide the collection tubes such that the closures are pierced in the appropriate locations near their centers. In addition, because the ribs are flexible, they allow the insertion and retention of a number of sizes of tubes, ranging from those having a small diameter to a relatively large diameter. The ribs will simply flex proportionally to the diameter of the collection tube inserted. If the tube has a closure having a large diameter than the tube itself, the ribs will flex proportionally to this larger diameter.

Figure 6:
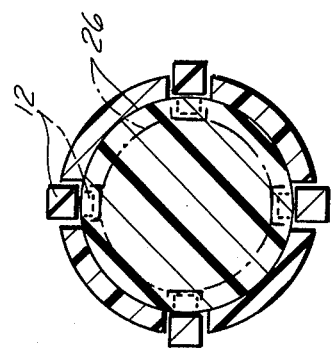
FIG. 6 is a cross-sectional view taken along line 6—6 of FIG. 4, and shows the relative deflection of ribs upon the insertion of tubes of various diameters.
Figure 7:
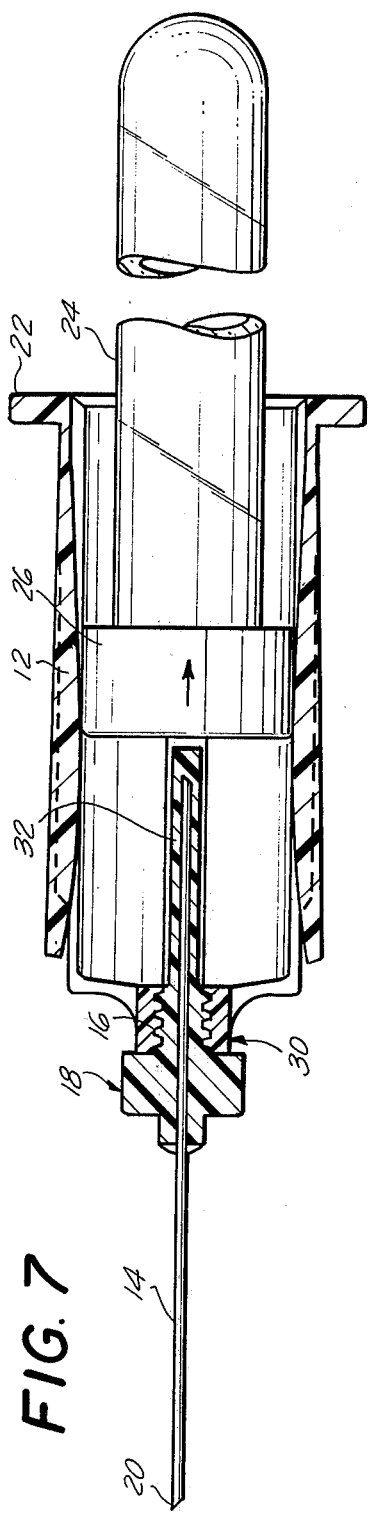
FIG. 7 is similar to FIG. 5, and shows the withdrawal of the evacuated tube.
Figure 3:
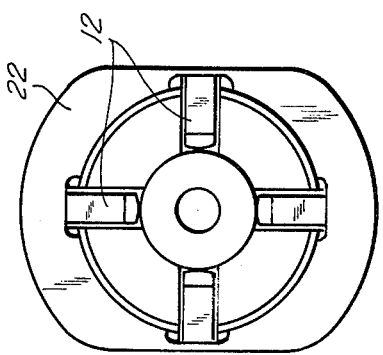
FIG. 3 is a frontal view of the invention taken along line 3—3 of FIG. 2.

FIGS. 2 and 6 illustrate the deflection of the ribs in the first-described embodiment. As shwon in FIG. 2, the tube and closure of smaller diameter will contact the ribs further into the barrel than the larger one. The deflection of the ribs will also be greater with the larger tube, as shown in FIG. 6. The movement of the ribs upon the insertion of a tube is clearly shown in FIG. 7.

Figure 11:
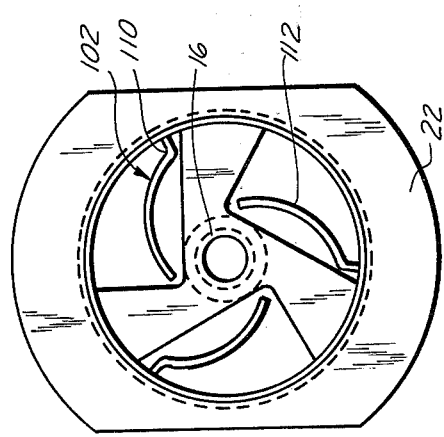
FIG. 11 is a rear view of the invention taken along line 11—11 of FIG. 10 prior to insertion of an evacuated tube.

In a similar manner, FIG. 13 shows the relative deflection caused by tubes of various diameters as compared with the undeflected ribs of FIG. 11.

The advantages of the novel holder over presently known devices are substantial. Because it is capable of accommodating tubes of different diameters, the user of the device need not make a plurality of venipunctures to fill these tubes. Only one venipuncture is necessary as the holder is "universal" for the various diameter tubes. This minimizes patient discomfort while expediting the blood sampling process. Manufacturing cost are also reduced as the universal holder takes the place of several different sized holders. It is also now possible to manufacture the smaller evacuated tubes with smaller closures or stoppers, as it is unnecessary to have a large outside diameter to contact the walls of a relative large holder.

In operation, the needle assembly 18 is attached to the holder 10 or 100 by means of the threaded portion 16. The cannula 14 is then injected into a fluid-containing part of the body, such as a vein. After venipuncture, the elastomeric sleeve 32 prevents the immediate flow of blood by occluding the open distal end 28 of the cannula 14. Referring to FIGS. 1-8, an evacuated tube 24 is then inserted within the holder 10, the ribs 12 deflecting about their points of hinged attachment 34 adjacent the flange to hold, center, and guide the tube. Because the ribs deflect in this manner, they are able to accomodate any number of differently sized evacuated tubes. Centering and guiding was found to be improved by utilizing a relatively short holder length of about 2.0 inches as compared with a larger length of about 2.4 inches.

The tube is fully inserted whereupon its stopper 26 is penetrated by the distal end of the cannula. FIGS. 4 and 5 show the compression of the sleeve 32 such that the end 28 establishes fluid communication between the interiors of the tube and the cannula. Due to the negative pressure from the vacuum, blood is drawn into the tube.

If the user wished to obtain an additional blood sample using a different size tube than the first, it was previously necessary for the needle to be withdrawn as conventional holders would not accomodate more than one size tube. However, using the universal holder, the different sized tube may now be employed using the same venipuncture. The first tube is simply withdrawn, and the second is inserted. The elastic sleeve occludes the open end during the change of tubes to prevent spillage of blood.

The universal holder 100 and flexible ribs 102 shown in FIGS. 9-13 function in a similar manner. Only the distal ends of the ribs are tapered in this embodiment, and the ribs will ordinarily deflect in the manner shown in FIG. 13. The tapering facilitates the insertion of the tube into the holder.

It is readily apparent that the universal holder provides significant advantages over conventional holders presently in use. As previously mentioned, different sized collection tubes having different sized closures may be filled using the same one venipuncture. This feature is helpful im minimizing patient discomfort while expediting the blood sampling process. Manufacturing costs are also reduced as the universal holder takes the place of several different sized holders. It is also now possible to manufacture the smaller evacuated tubes with smaller stoppers, as it is unnecessary to have a large outside diameter to contact the walls of a relatively large holder.

Although the embodiments as described above contain features which are particularly advantageous for accommodating collection tubes of various sizes, other embodiments may also be utilized for this purpose. Ribs or other quivalent resilient means may be inclined which deform or flex in other directions, and the number of ribs may be other than the three or four shown in the drawings. The holder may also be adapted for accomodating needle assemblies of various constructions. Accordingly, the scope of the invention should be determined by the appended claims.

What is claimed is:

1. A holder capable of holding body fluid collection containers of various diameters, said holder comprising:
   a housing having a forward end and a rear end, said forward end being adapted to accommodate a needle assembly having a first end designed for penetration of the body and a second end designed for penetration of a closure of an evacuated collection container, and said rear end adapted for the insertion of a fluid collection container; and
   a plurality of deformable ribs attached to and disposed inwardly of the housing, said ribs being able to frictionally engage collection containers of various diameters.

2. A holder as described in claim 1 wherein the ribs are tapered inwardly in the direction of the forward end of the housing to guide and center an evacuated collection container while facilitating its insertion in the holder.

3. A holder as described in claim 1 wherein the ribs are attached only near the rear end of the housing, said ribs extending inwardly in the direction of the forward end and being deflectable about their points of attachment to the housing.

4. A holder as described in claim 1 wherein the ribs have a spiral configuration.

5. A holder as described in claim 1 wherein the holder includes at least three ribs.

6. A holder as described in claim 1 wherein the housing is cylindrical for accomodation of tubular shaped evacuated collection containers.

7. A holder as described in claim 6 wherein the forward end of the housing is threaded for accomodation of a needle assembly and the rear end is flanged to facilitate gripping.

8. A device for the collection of body fluids comprising:
   a needle assembly having a first end designed for penetration of a patient and a second end adapted for penetration of a closure of a body fluid collection container; and
   a holder having a forward end attached to said needle assembly, an open rear end designed for insertion of a body fluid collection container, and deformable ribs attched to and disposed inwardly of the holder so as to be able to frictionally engage collection containers of various diameters.

9. A device as described in claim 8 wherein the needle assembly has a cannula attached to its first end adapted for intravenous pentration.

10. A device as described in claim 8 wherein the ribs are tapered inwardly in the direction of the forward end of the housing to center, guide, and facilitate insertion of a body fluid collection container.

11. A device as described in claim 8 wherein the ribs are attached only near the rear end of the holder, said ribs extending inwardly in the direction of the forward end and being deflectable about their points of attachment to the holder.

12. A device as described in claim 8 wherein the ribs have a spriral configuration.

13. A device as described in claim 8 wherein the holder includes at least three ribs.

14. A device as described in claim 8 wherein the holder is cylindrical for accomodation of tubular shaped fluid collection containers.

15. A holder for body fluid collection containers comprising a barrel and means for varying the cross-sectional area of the interior of the barrel for accomodating collection containers of various diameters.

16. A holder as described in claim 15 wherein the means for varying the cross-sectional area of the barrel assumes a first position of minimum cross-sectional area, said means being adjustable to assume any one of several positions between the minimum cross-sectional area to the area defined by the inside diameter of the barrel.

17. A holder as described in claim 15 wherein the means for varying the cross-sectional area is resiliently biased inwardly to grip an inserted collection container.

18. A holder as described in claim 15 wherein the barrel is cylindrical for the accomodation of tubular collection containers.

19. A tube holder comprising an elongate body member having a chamber for selectively receiving blood collection containers of different sizes, said body member having means at the distal end thereof for supporting a double-ended needle cannula with the cannula having a distal end portion external to said chamber for insertion into a body vessel and a proximal end portion extending proximally into said chamber for piercing a stopper of a collecting container when inserted into said chamber, said chamber having resilient walls adapted to be engaged by a collection container for guiding the collection container centrally toward the distal end of said body member such that the proximal portion of the needle enters the central portion of the stopper, said resilient walls extending distally substantially from the proximal end of said chamber to the distal end of said chamber and being normally inclined from their proximal ends toward the longitudinal axis of said body member.

20. The tube holder of claim 19 wherein said resilient walls are circumferentially spaced about said body member and connected to said body member at their proximal ends.

21. The tube holder of the claim 20 wherein said body member has fixed longitudinally extending portions circumferentially alternating with said resilient walls.

22. The tube holder of claim 19 wherein said supporting means includes a threaded hole in the distal end of said body member for threadedly receiving a double-ended needle assembly.

23. A tube holder comprising a barrel member of plastic material defining a chamber for selectively receiving and guiding for movement blood collection tubes of different sizes, said chamber being open at the proximal end for receiving a blood collection tube, said barrel member having an end wall at the distal end thereof engageable with a blood collection tube, said end wall including coupling means for connecting a double-ended needle cannula thereto substantially coincident with the longitudinal axis of said barrel and with a portion extending proximally from said end wall, said barrel member having a plurality of circumferentially spaced elongate flexible tube guide arms connected at their proximal ends to the proximal end portion of said barrel member, the longitudinal axis of each of said guide arms when the guide arms are unstressed by a blood collection tube being at an angle to the longitudinal axis of said barrel, said guide arms being resiliently urged radially outwardly upon engagement with a blood collection tube inserted into said barrel to guide the same toward the distal end of said chamber with the collection tube substantially concentric with said barrel whereby the needle portion pierces a central portion of the tube stopper.

24. The tube holder of claim 23 wherein said body member has a radially outwardly extending finger flange at the proximal end of said body member.

* * * * *